United States Patent
Echegaray et al.

(10) Patent No.: US 6,333,411 B1
(45) Date of Patent: Dec. 25, 2001

(54) METHOD FOR PRODUCTION OF HYDROXYLAMMONIUM PHOSPHATE IN THE SYNTHESIS OF CAPROLACTAM

(75) Inventors: Diego Fernandez Echegaray; Antonio Augusto M. Velloso, both of Salvador, Bahia (BR); Matthew Lincoln Wagner, White Plains, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/221,211

(22) Filed: Dec. 24, 1998

(51) Int. Cl.$^7$ .................................................. C07D 201/04
(52) U.S. Cl. ..................... 540/535; 423/400; 423/405; 540/536
(58) Field of Search ..................... 540/535, 536; 423/392, 393, 400, 405

(56) References Cited

U.S. PATENT DOCUMENTS

| 3,720,755 | 3/1973 | Duyverman et al. | 423/307 |
| 4,183,906 | 1/1980 | Watson et al. | 423/392 |
| 4,235,858 | 11/1980 | Blakey et al. | 423/393 |
| 5,777,163 | 7/1998 | Müller et al. | 564/301 |
| 5,985,230 * | 11/1999 | Vlaming et al. | 423/392 |

FOREIGN PATENT DOCUMENTS

| 0194715 | 9/1986 | (EP) . | |
| 0799794 A1 | 10/1997 | (EP) . | |
| 1539288 | 8/1968 | (FR) . | |
| 803211 * | 10/1958 | (GB) | 423/392 |

OTHER PUBLICATIONS

A. H. de Rooij et al., "XP–000984617 Caprolactime le Procédé HPO", Informations Chimie no 165–Avril 1977–121 (no month).

E. Faried et al.,"Boosting Existing Nitric Acid Production", The Fertiliser Society of London—Oct. 16, 1986.

A. H. de Rooij et al., "XP–002133389 Caprolactam, the HPO process", Chemical Abstracts, vol. 87 Nov. 07, 1977, No. 2 ( no month).

* cited by examiner

Primary Examiner—Wayne Langel
(74) Attorney, Agent, or Firm—Bernard Lau

(57) ABSTRACT

A method for production of caprolactam. The method involves:

(a) reacting air with ammonia gas in an ammonia conversion zone to produce nitric oxide;

(b) oxidizing at least a portion of the nitric oxide to nitrogen dioxide to produce an $NO_x$-rich process gas stream;

(c) reactively absorbing the $NO_x$-rich gas stream with phosphoric acid containing solution in an absorption zone to form nitrate ions;

(d) contacting the nitrate ions with air in a degassing zone to produce a nitrate-rich aqueous process stream;

(e) reducing the nitrate-rich aqueous stream with hydrogen in the presence of phosphoric acid to produce hydroxylammonium phosphate;

(f) oximating the hydroxylammonium phosphate with cyclohexanone to produce cyclohexanone oxime; and (g) converting the cyclohexanone oxime to caprolactam.

According to the invention, supplemental oxygen is added downstream of the ammonia conversion zone to increase the quantity and rate of formation of nitrogen dioxide in the $NO_x$-rich process gas stream.

6 Claims, 2 Drawing Sheets

METHOD FOR PRODUCTION OF HYDROXYLAMMONIUM PHOSPHATE IN THE SYNTHESIS OF CAPROLACTAM

BACKGROUND OF THE INVENTION

Caprolactam can be produced from three hydrocarbon feedstocks: cyclohexane, phenol, and toluene. Approximately 68% of the world's caprolactam capacity is produced from cyclohexane, 31% from phenol, and 1% from toluene. All of the cyclohexane and phenol-based production proceeds via the formation of cyclohexanone oxime. In 94% of the cyclohexane and phenol-based caprolactam capacity, the formation of this oxime requires an ammonia oxidation step.

In the processes involving ammonia oxidation, caprolactam production from cyclohexane or phenol can be broken down into the following steps:

Oxidation of cyclohexane or hydrogenation of phenol, to synthesize cyclohexanone;

Oxidation of ammonia to form nitric oxide, followed by various reaction steps to form a hydroxylamine salt;

Synthesis of cyclohexanone oxime by reaction of cyclohexanone and the hydroxylamine salt; and Treatment of the cyclohexanone oxime with sulfuric acid followed by neutralization with aqueous ammonia to form caprolactam.

One such method for producing caprolactam is the DSM-HPO (Dutch State Mines-Hydroxylammonium Phosphate-Oxime) process, also known as the Stamicarbon process. Such process is disclosed, for example, in Weissermel and Arp, Industrial Organic Chemistry (VCH Verlagsgesellschaft mbH 1993), pp. 249–258. In the DSM-HPO process, hydroxylammonium phosphate ($NH_3OH.H_2PO_4$) is reacted with cyclohexanone in toluene solvent to synthesize the oxime.

The hydroxylammonium phosphate is synthesized in the DSM-HPO process in the following manner:

Catalytic air oxidation of ammonia to form nitric oxide:

$$4\ NH_3 + 5\ O_2 \rightarrow 4\ NO + 6\ H_2O \quad (I)$$

Continued oxidation of nitric oxide to form nitrogen dioxide, among other nitrogen oxides:

$$NO + \tfrac{1}{2}\ O_2 \rightarrow NO_2 \quad (II)$$

Reactive absorption of nitrogen dioxide in a buffered aqueous phosphoric acid solution to form nitrate ions:

$$3\ NO_2 + H_2O \rightarrow 2\ HNO_3 + NO \quad (III)$$

$$HNO_3 + H_2PO_4 \rightarrow NO_3 + H_3PO_4 \quad (IV)$$

Catalytic hydrogenation of nitrate ions to form hydroxylammonium phosphate:

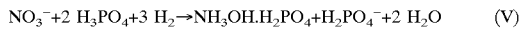

$$NO_3^- + 2\ H_3PO_4 + 3\ H_2 \rightarrow NH_3OH.H_2PO_4 + H_2PO_4^- + 2\ H_2O \quad (V)$$

Oximating the cyclohexanone with hydroxylammonium phosphate to produce cyclohexanone oxime:

$$C_6H_{10}O + NH_3OH.H_2PO_4 \rightarrow C_6H_{11}NO + H_3PO_4 + H_2O \quad (VI)$$

The process for forming hydroxylammonium phosphate in the DSM-HPO process is shown in the flow sheet depicted in FIG. 1 of the attached drawing. As shown therein, an air stream 3 is initially compressed in a compressor 10, introduced as a "primary" air stream through feed line 12 into admixture with a gaseous ammonia stream 1, and thereafter fed to a catalytic ammonia converter 20. Typically, 100% ammonia conversion and 95% selectivity to NO are achieved in that reaction. Upon exiting the converter, some of the NO is further oxidized to $NO_2$ to form an $NO_x$-rich process gas stream 15. Some of the $NO_2$ in the $NO_x$-rich process stream 15 dimerizes to form $N_2O_4$.

The $NO_x$-rich process gas stream 15 is contacted countercurrently with an aqueous inorganic acid stream 37 in a trayed absorption tower 40. In the conventional DSM-HPO process, a "secondary" air stream 11 is added into a degasser 50 in amounts of from 5 to 20 volume % of the total air flow to the system. The secondary air stream 11 becomes laden with nitric oxide and the resulting nitric oxide laden air stream 17 is added to the base of the absorption tower 40. A nitrate-rich liquid stream 13 exiting the absorption tower 40 is routed to the degasser 50, and an NO, containing vent gas 5 exits the absorption tower.

The vent gas 5 exiting the absorption tower 40 must normally be properly regulated to minimize the emission of $NO_x$. An increase in production of hydroxylammonium phosphate typically results in a corresponding increase in $NO_x$ emission in the vent gas 5.

The aqueous inorganic acid stream 37 added to the top of the absorption tower 40 contains a mixture of water, phosphoric acid ($H_3PO_4$), ammonium nitrate ($NH_4NO_3$), and monoammonium phosphoric acid ($NH_4H_2PO_4$). The acid stream 37 is continuously cycled from the oximator train (consisting of an oximator 70, oxime extractor 80, and a hydrocarbon stripper 90) to the hydroxylamine train (consisting of the absorption tower 40, degasser 50, and a nitrate hydrogenator 60). Nitric oxides in the $NO_x$-rich process gas stream 15 reactively absorb in the phosphoric acid solution in the absorption tower 40 to form nitrate ions.

The nitrate-rich liquid stream 13 exiting the absorption tower 40 is passed through the degasser 50, where it is contacted countercurrently with secondary air 11 entering the degasser 50. The secondary air 11 removes unreacted nitric oxides from the nitrate-rich liquid stream 13. The nitric oxide-containing air stream 17 exiting the degasser 50 is routed to the absorption tower 40.

A nitrate-rich liquid stream 19 exiting the degasser 50 is combined with an aqueous inorganic acid stream 21 from the oximator train, and the combination 31 fed to the nitrate hydrogenator 60. A hydrogen stream 7 is also added to the nitrate hydrogenator 60. Nitrate ions are reduced with hydrogen in the nitrate hydrogenator 60 over a palladium catalyst to form hydroxylammonium phosphate. An aqueous stream of hydroxylammonium phosphate, phosphoric acid, ammonium nitrate, and monoammonium phosphoric acid 23 exits the nitrate hydrogenator 60.

The hydroxylammonium phosphate containing aqueous stream 23 then reacts with a stream of cyclohexanone in toluene solvent 25 in the oximator 70 to produce cyclohexanone oxime. An oxime-toluene stream 9 exits the oximator 70 and is processed into caprolactam. An aqueous stream 27 also exits the oximator 70, and is routed to a oxime extractor 80 which removes entrained oxime 39, and adds it to the stream of cyclohexanone in toluene solvent 25. An aqueous stream 29 exiting the oxime extractor 80 is routed to a hydrocarbon stripper 90 where entrained cyclohexanone and toluene 33 are removed and added to the stream of cyclohexanone in toluene solvent 25, which is routed to the oximator 70. Thus, the entrained oxime 39 obtained in the oxime extractor 80 and the cyclohexanone-toluene 33 obtained in the hydrocarbon stripper 90 are returned to the oximator 70. The aqueous stream 35 leaving the hydrocarbon stripper 90 is routed back to the hydroxylamine train, where a portion 21 is distributed to the nitrate hydrogenator 60 and a portion 37 is distributed to the absorption tower 40. Typically, about 90% of aqueous stream 35 is routed to stream 21, and about 10% routed to stream 37.

In view of the strict environmental regulation of $NO_x$ emissions, the quantity of $NO_x$ in the vent gas 5 cannot be increased. Accordingly, any increased hydroxylammonium phosphate production (and subsequent caprolactam production) must be obtained without any increase in $NO_x$ emissions. This can be accomplished by increasing the amount of air and ammonia fed to the process while increasing the plant size, e.g., the size of the absorption tower 40 and air compressor 10. However, such an increase in equipment capacity requires substantial capital investment.

There is therefore a need for the development of improved techniques in the DSM-HPO process for producing caprolactam, by which increased amounts of hydroxylammonium phosphate and, consequently, caprolactam can be produced without large capital investment, and without increasing $NO_x$ emissions.

SUMMARY OF THE INVENTION

The present invention provides an improvement in the DSM-HPO process for production of caprolactam involving:

(a) reacting air with ammonia gas in an ammonia conversion zone to produce nitric oxide;

(b) oxidizing at least a portion of the nitric oxide to nitrogen dioxide to produce an $NO_x$-rich process gas stream;

(c) reactively absorbing the $NO_x$-rich gas stream with phosphoric acid containing solution in an absorption zone to form nitrate ions;

(d) contacting the nitrate ions with air in a degassing zone to produce a nitrate-rich aqueous process stream;

(e) reducing the nitrate-rich aqueous stream with hydrogen in the presence of phosphoric acid to produce hydroxylammonium phosphate;

(f) oximating the hydroxylammonium phosphate with cyclohexanone to produce cyclohexanone oxime; and (g) converting the cyclohexanone oxime to caprolactam.

In accordance with the invention, the foregoing process is improved by adding supplemental oxygen downstream of the ammonia conversion zone to increase the quantity and rate of formation of nitrogen dioxide in the $NO_x$-rich process gas stream.

Desirably, a portion of secondary air, normally introduced into the degassing zone is rerouted to the ammonia conversion zone to increase the production of nitric oxide formed in the ammonia conversion zone without increasing the level of $NO_x$ contained in the gas vented from the absorption zone.

Utilizing the improved technique of the invention, desirably by rerouting a portion of the secondary air to the ammonia conversion zone and maintaining the volumetric percentage of ammonia fed to the conversion zone at a constant or increased level, the production of NO in the ammonia conversion zone is increased. By adding supplemental oxygen according to the invention, both the amount and rate of conversion of NO to $NO_2$ are increased, thereby promoting formation of nitrate in the absorption zone, without any adverse effect on the $NO_x$ content of gases vented from the absorption zone. Alternatively, the addition of supplemental oxygen may be used to lower $NO_x$ emissions, with or without rerouting of secondary air to the ammonia conversion zone, and with or without increases in nitrate (and consequently hydroxylammonium phosphate and caprolactam) production. The invention also encompasses adding supplemental oxygen according to the invention without rerouting a portion of secondary air to the ammonia converter, but increasing the volumetric percentage of ammonia fed to the conversion zone to increase production of NO. This ultimately results in an increase in formation of hydroxylammonium phosphate and caprolactam without an increase in $NO_x$ emissions.

The method of the present invention thus facilitates an increase in hydroxylammonium phosphate production in the DSM-HPO process for synthesizing caprolactam, while maintaining $NO_x$ emissions at constant, or decreased, levels. It is estimated that use of the method of the invention normally results in an increase of between about 5 and 15% in the production of hydroxylammonium phosphate without increasing $NO_x$ emissions. Furthermore, this is accomplished without substantial capital investment, such as would otherwise be required to increase plant capacity. Moreover, by substituting oxygen for inert nitrogen present in the secondary air conventionally fed to the absorption zone, the oxygen partial pressure in the system may be increased and residence times for the intermediates formed in the various stages of the process may be lowered.

In the production of nitric acid, it is known that direct injection of supplemental oxygen can boost nitric acid synthesis while controlling $NO_x$ emissions.

Such addition of oxygen is described, for example, in U.S. Pat. Nos. 4,183,906; 4,183,906; 4,235,858; and 5,167,935; UK Patent No. 803211; and EP published Patent Applications Nos. 799794 and 808797. Oxygen addition is also described in Kongshaug, Extension of Nitric Acid Plant Capacity by Use of Oxygen, Nitric Acid Symposium (1981); and by Faried et al., Boosting Existing Nitric Acid Production, The Fertiliser Society (1986). For example, EP 808797 describes an improved process for nitric acid production in which supplemental oxygen is added to the cooler/condenser, the absorption tower, the ammonia converter, and/or the bleacher, to cause an increase in nitric acid production without increasing NO, emissions. No supplemental oxygen addition of this type is believed to have been previously disclosed in connection with the synthesis of caprolactam.

Feeding oxygen to the ammonia converter has been employed in the BASF and Inventa processes for the synthesis of caprolactam. (See Kirk Othmer Encyclopedia of Chemical Technology, 4th Edition, 4: 831 (1992); U.S. Pat. No. 5,777,163.) In these processes, however, no supplemental oxygen is added downstream of the converter. Also, the BASF and Inventa processes differ substantially from the DSM-HPO process for producing caprolactam in that they do not add air to the ammonia converter, and do not involve the formation of intermediates analogous to those produced in the DSM-HPO process.

DETAILED DESCRIPTION OF THE INVENTION

All patent applications, patents, and literature references cited in this specification are hereby incorporated by reference in their entirety.

In accordance with the present invention, a supplemental oxygen stream 43, (see FIG. 2) is injected downstream of the ammonia converter 20 of the hydroxylammonium phosphate reaction train (FIG. 2) in the DSM-HPO process for the synthesis of caprolactam.

As used herein, the term "supplemental oxygen" refers to pure oxygen or any oxygen-enriched gaseous stream containing more than about 50%, and preferably more than about 90%, oxygen by volume. Suitable supplemental oxygen sources include pipeline oxygen, independent cryogenic oxygen plants or PSA/VPSA oxygen plants, liquid oxygen tanks or oxygen-enriched air streams.

Figure 1:
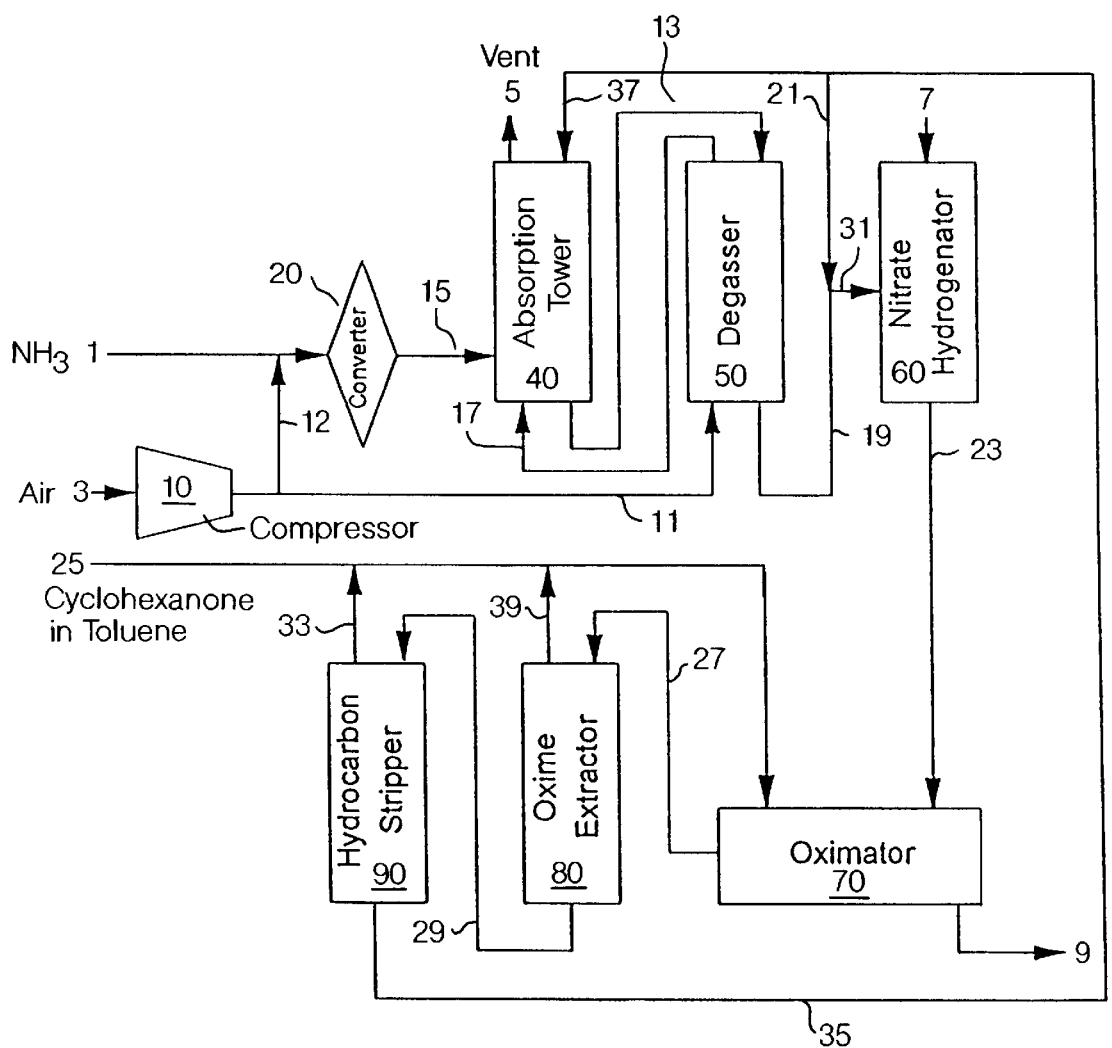
FIG. 1 is a schematic flow sheet of the portion of the prior art DSM-HPO process for production of caprolactam that results in production of cyclohexanone oxime.

The supplemental oxygen is desirably injected in place of at least a portion of the secondary air introduced to the degasser in the DSM-HPO process through line 11 (FIG. 1). In accordance with a preferred embodiment of the present invention, air that would otherwise have been employed as "secondary" air is instead fed through feed line 12 for introduction as primary air into the ammonia converter 20. Gaseous mixtures containing about 8 to 12 mole % ammonia and about 18 to 20 mole % oxygen are thus introduced into the ammonia converter, and converted therein under the reaction conditions, e.g., temperature, pressure and catalyst, utilized in the DSM-HPO process to produce gaseous reaction mixtures containing in mole %, about:

7 to 12% NO
11 to 18% $H_2O$
67 to 72% $N_2$
3 to 10% $O_2$

By thus increasing the flow of primary air introduced into the ammonia converter, the amount of NO formed therein is increased by about 5 to 15% as compared with the ammonia oxidation step in the absence of the addition of supplemental oxygen according to the invention.

The supplemental oxygen is preferably added to the absorption zone in the proportion of about 1.8 to 4.0 moles of $O_2$ per mole of incremental NO produced in the ammonia converter (i.e., per mole of additional NO produced as a result of oxygen addition according to the invention). By thus increasing the amount of oxygen introduced into the absorption zone, both the quantity and rate of formation of $NO_2$ and nitrate ions are enhanced.

Figure 2:
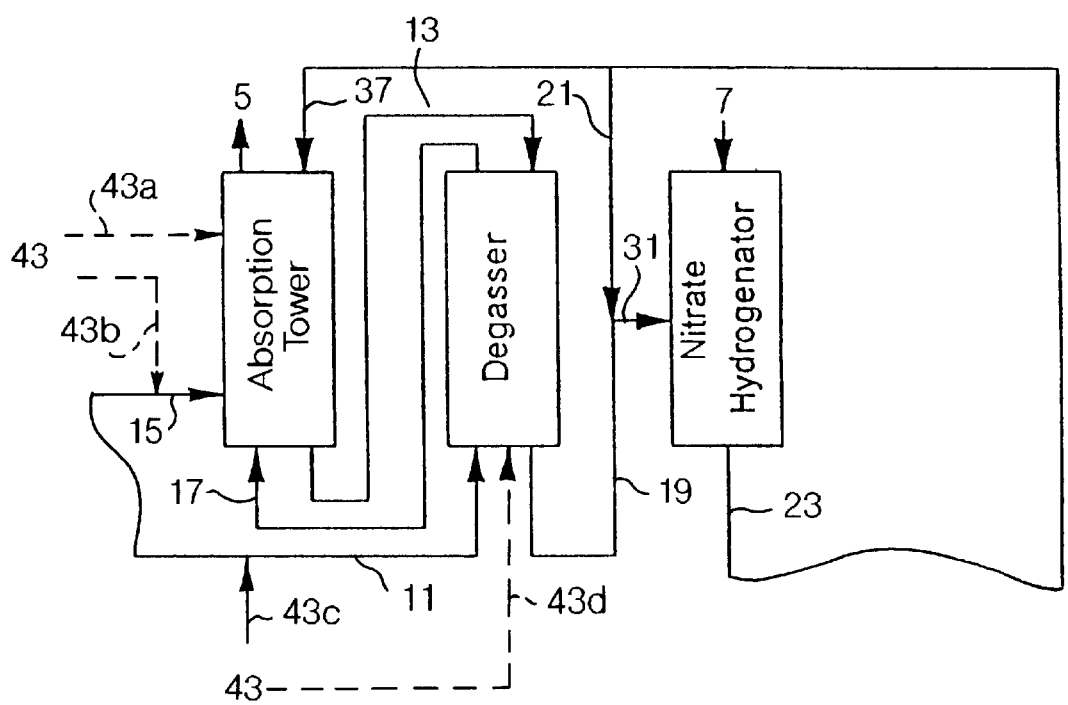
FIG. 2 is a schematic flow sheet depicting a portion of DSM-HPO process as modified in accordance with the invention.

FIG. 2 shows the portion of the process for producing caprolactam by the DSM-HPO method to which the present invention relates. According to the invention, oxygen is injected in the process for hydroxylammonium phosphate synthesis, downstream of the reaction of air with ammonia gas. The invention encompasses injection of oxygen in any manner that increases the formation of $NO_2$, thereby decreasing the amount of $NO_x$ that would otherwise be emitted.

The supplemental oxygen may be added through any of the alternative streams shown in FIG. 2. For example, in one embodiment of the invention the supplemental oxygen stream 43 is injected via line 43b into the process gas line 15 entering the absorption tower 40. Alternatively, the supplemental oxygen 43 may be injected through line 43a directly into the absorption tower 40. It is also feasible to inject the supplemental oxygen 43 into the degasser via line 43c into process gas line 11 supplying secondary air to the degasser, or inject the supplemental oxygen 43 via line 43d directly into the degasser. The invention also encompasses the direct addition of the supplemental oxygen at several locations in the absorption tower and the degasser. The supplemental oxygen is preferably introduced under positive pressures of between about 2 and 20 psig, typically about 5 psig.

As noted above, practice of the improved method of this invention does not involve any capital investment of the order of that which would be required to, e.g., expand the capacity of the absorption tower. Furthermore, retrofitting of existing plants to practice the improved technique of the invention can be easily carried out by providing the necessary supplemental oxygen supply lines and connecting them by conventional means to the relevant process line or process unit as outlined above.

The invention is further illustrated by the following example, which is intended to exemplify practice of the invention, and not to be construed as limiting its scope.

Example

The method of the invention was employed to modify an existing caprolactam production plant using the DSM-HPO process wherein the upper section of the absorber had been damaged. This, in turn, reduced the ability of the absorber to reoxidize NO to $NO_2$, and to absorb nitrate ions. Thus, production was limited, and $NO_x$ emissions increased.

The method of the invention was employed in this process to increase hydroxylammonium phosphate production and to lower $NO_x$ emissions. Specifically, oxygen was injected via a sparger into the nitrate-rich liquid in the degassing tower. A portion of the secondary air that would otherwise have been fed to the degasser was rerouted to the converter, and the amount of ammonia fed to the converter increased The table below shows the amounts of oxygen and ammonia added in seven tests that were run. The "secondary air flow", "$NH_3$ Flow", and "$NO_x$ in vent gas" values shown represent the percent changes relative to the DSM-HPO process as operated without oxygen injection according to the invention. The percent increase in hydroxylammonium phosphate achieved using the method of the invention was the same as the percent increase in $NH_3$ flow shown. The "$O_2/NH_3$ added" values shown indicate the molar ratio of oxygen injected to $NH_3$ flow.

| Test | 1 | 2 | 3 | 4 | 5 | 6 | 7 |
|---|---|---|---|---|---|---|---|
| Second Air Flow | −49% | −50% | −51% | −100% | −100% | −100% | −94% |
| $NH_3$ Flow | +5.7% | +5.6% | +5.6% | +9.5% | +9.8% | +9.3% | +8.2% |
| $O_2$/ added $NH_3$ | 3.2 | 3.2 | 3.2 | 3.3 | 3.2 | 3.3 | 3.8 |
| $NO_x$ in vent gas | NA | −24% | −43% | NA | −2% | NA | NA |

Thus, in these tests from about 50% to 100% of the secondary air was diverted from the degasser to the converter. Oxygen was added according to the present invention at a rate of from 3.2 to 3.8 moles of oxygen per mole of added ammonia. The oxygen addition removed dissolved $NO_2$ from the nitrate-rich stream, thereby promoting increased oxidation of NO to $NO_2$, and an increase in hydroxylammonium phosphate production of up to 9.8%. Furthermore, the increase in hydroxylammonium phosphate production was achieved without an increase in $NO_x$ content in the vent gas.

While preferred embodiments of the process hereof are described hereinabove, it will be apparent to those skilled in the art that various changes may be made therein without departing from the scope of the invention as defined in the claims appended hereto.

We claim:

1. In a method for production of caprolactam which comprises:
   (a) reacting air with ammonia gas in an ammonia conversion zone to produce nitric oxide;
   (b) oxidizing at least a portion of the nitric oxide to nitrogen dioxide to produce an $NO_x$-rich process gas stream;
   (c) reactively absorbing the $NO_x$-rich gas stream with phosphoric acid containing solution in an absorption zone to form nitrate ions;
   (d) contacting the nitrate ions with air in a degassing zone to produce a nitrate-rich aqueous process stream;
   (e) reducing the nitrate-rich aqueous stream with hydrogen in the presence of phosphoric acid to produce hydroxylammonium phosphate;
   (f) oximating the hydroxylammonium phosphate with cyclohexanone to produce cyclohexanone oxime; and
   (g) converting the cyclohexanone oxime to caprolactam;

the improvement comprising adding supplemental oxygen downstream of the ammonia conversion zone while simultaneously rerouting a portion of the secondary air to the ammonia conversion zone and increasing the amount of ammonia gas added to the ammonia conversion zone to increase the production of nitric oxide formed in the ammonia conversion zone and the quantity and rate of formation of nitrogen dioxide in the absorption zone.

2. The method of claim 1 wherein the supplemental oxygen is added into a secondary air stream providing air to the degassing zone.

3. The method of claim 1 wherein the supplemental oxygen is added directly into the degassing zone.

4. The method of claim 1 wherein the supplemental oxygen is added directly into the absorption zone.

5. The method of claim 1 wherein the supplemental oxygen is added to the NOx-rich process gas stream upstream of the absorption zone.

6. The method of claim 1 wherein the supplemental oxygen is a gas comprising more than about 90 vol. % oxygen.

* * * * *